(12) United States Patent
Abdul

(10) Patent No.: US 8,241,565 B1
(45) Date of Patent: Aug. 14, 2012

(54) SHOE SOLE SANITIZING DEVICE AND ASSOCIATED METHOD FOR ERADICATING MICROORGANISMS FROM AN EXTERIOR SURFACE OF A SHOE SOLE

(76) Inventor: Bibi Rabbia Abdul, Garden City, NY (US)

( * ) Notice: Subject to any disclaimer, the term of this patent is extended or adjusted under 35 U.S.C. 154(b) by 329 days.

(21) Appl. No.: 12/543,212

(22) Filed: Aug. 18, 2009

Related U.S. Application Data

(60) Provisional application No. 61/189,267, filed on Aug. 18, 2008.

(51) Int. Cl.
*A61L 2/00* (2006.01)

(52) U.S. Cl. ............... 422/24; 422/186.3; 250/455.11; 607/94

(58) Field of Classification Search ............... 422/3, 5, 422/20–24, 26–37; 250/365, 455.11, 492.1, 250/504 R; 607/88, 94
See application file for complete search history.

(56) References Cited

U.S. PATENT DOCUMENTS

| | | |
|---|---|---|
| 2,246,135 A | 6/1941 | James |
| 2,350,091 A | 5/1944 | Bergman |
| 2,413,494 A | 12/1946 | Fortney |
| 4,981,651 A | 1/1991 | Horng |
| 5,820,821 A | 10/1998 | Kawagoe |
| 5,978,996 A | 11/1999 | Ullman |
| 7,875,869 B1 * | 1/2011 | Shadan ............... 422/24 |
| 2001/0010806 A1 | 8/2001 | Kanazawa |
| 2002/0083535 A1 | 7/2002 | Fraden |
| 2009/0117001 A1 * | 5/2009 | Hyde et al. ............... 422/24 |
| 2009/0314308 A1 * | 12/2009 | Kim et al. ............... 250/492.1 |

OTHER PUBLICATIONS

Ivnitski et al., "Biosensors for detection of pathogenic bacteria." Biosensors and Bioelectronics. 14 (1999) 599-624.*

* cited by examiner

*Primary Examiner* — Walter D Griffin
*Assistant Examiner* — Timothy Cleveland

(57) ABSTRACT

A shoe sole sanitizing device preferably includes a portable platform including a pair of shoe sole-receiving sections including open bottom surfaces respectively. Each of the shoe sole-receiving sections may be adapted to receive the exterior sole of the shoe thereon. The portable platform may further include a plurality of disposable transparent stratums removably positioned on the open bottom surfaces respectively. A plurality of ultraviolet light emitting sources are aligned beneath the shoe sole-receiving sections respectively. Notably, a mechanism is also provided for independently toggling each of the ultraviolet light emitting sources between on and off modes upon detecting a corresponding triggering event respectively. The ultraviolet light emitting sources upwardly emit an array of ultraviolet light towards the transparent stratums respectively such that the ultraviolet light arrays penetrate through the disposable transparent stratums and eradicate microorganisms deposited on the exterior surface of the shoe sole.

12 Claims, 3 Drawing Sheets

SHOE SOLE SANITIZING DEVICE AND ASSOCIATED METHOD FOR ERADICATING MICROORGANISMS FROM AN EXTERIOR SURFACE OF A SHOE SOLE

CROSS REFERENCE TO RELATED APPLICATIONS

This application claims the benefit of U.S. Provisional Application No. 61/189,267, filed Aug. 18, 2008, the entire disclosures of which are incorporated herein by reference.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to shoe sanitizing devices and, more particularly, to a shoe sanitizing device that selectively adjusts output durations of ultraviolet light emitting sources based upon an initial level of microorganisms detected on an exterior shoe sole.

2. Prior Art

It is well-known that exposure to ultraviolet (UV) light of certain wavelengths, intensities, and durations can destroy or inhibit growth of surface pathogens. For instance, germicidal lamps that emit UVC radiation are used to treat waste water for the purpose of reducing organic content. U.S. Pat. Nos. 4,981,651 and 5,978,996 describe the use of UV light for sterilization.

The UV spectrum spans wavelengths from 10 nm to 400 nm. The band from 320 nm to 400 nm is designated as UVA; 280 nm to 320 nm is UVB; and 185 nm to 280 nm is UVC. Germicidal UV light, the type that destroys microorganisms, is limited to a wavelength range from 240 nm to 280 nm, in which maximum germicidal efficiency coincides with a wavelength of 254 nm.

Various methods for disinfecting and removing odor from shoes are known in prior art. These include chemical and physical methods. More specifically, chemical methods include various sprays and shoe liners, while physical include irradiation of the shoe interior by UV light. The methods vary by convenience of application, cost, safety, duration of protection and other features.

The ultraviolet devices appear to be most efficient. However, they suffer from several disadvantages, including difficulty of selectively adjusting a duration of time in which the UV light is transmitted to the shoe. For example, prior art devices deliver UV light to the shoe for a predetermined period of time, regardless of the level of microorganisms located on the shoe. Such prior art shortcomings create the problem of ineffectively disinfecting the shoe and thereby requiring several repeated treatments.

Further, none of prior art eradicates microorganisms from an outer surface of an exterior shoe sole.

Accordingly, a need remains for shoe sanitizing device in order to overcome the above-noted shortcomings. The present invention satisfies such a need by providing a shoe sanitizing device that is convenient and easy to use, is durable yet lightweight in design, is versatile in its applications, and provides a mechanism for selectively adjusting a duration of time in which the UV light is transmitted to the shoe, based upon the microorganism level located on the shoe.

BRIEF SUMMARY OF THE INVENTION

In view of the foregoing background, it is therefore an object of the present invention to provide a shoe sole sanitizing device for disinfecting a bottom surface of an exterior sole of a shoe. These and other objects, features, and advantages of the invention are provided by a shoe sole sanitizing device preferably including a portable platform adapted to be placed on a ground surface. Such a portable platform may include a top plate provided with a pair of shoe sole-receiving sections including open bottom surfaces respectively. Each of the shoe sole-receiving sections may be adapted to receive the exterior sole of the shoe thereon, The portable platform may further include a plurality of disposable transparent stratums removably positioned on the open bottom surfaces respectively. A bottom plate is preferably connected to the top plate and remains disposed subjacent to the shoe sole-receiving sections. In this manner, a cavity formed between the top and bottom plate.

The present invention further includes a plurality of ultraviolet light emitting sources aligned beneath the shoe sole-receiving sections respectively. Notably, a mechanism is also provided for independently toggling each of the ultraviolet light emitting sources between on and off modes upon detecting a corresponding triggering event respectively. The ultraviolet light emitting sources upwardly emit an array of ultraviolet light towards the transparent stratums respectively such that the ultraviolet light arrays penetrate through the disposable transparent stratums and eradicate microorganisms deposited on the exterior surface of the shoe sole.

The independent toggling mechanism preferably includes a plurality of first sensors situated within the platform. Each of the first sensors generates and transmits a first pressure input signal when the shoe sole is positioned on a corresponding one of the shoe sole-receiving sections. Such first sensors further generate and transmit a second pressure input signal when the shoe sole is removed from the corresponding shoe sole-receiving section. Such second sensors may be biosensors, well understood by one skilled in the art.

The independent toggling mechanism further includes a plurality of second sensors situated within the platform. Such second sensors generate and transmit a first microorganism input signal that corresponds to an initial level of detected microorganisms before the ultraviolet light emitting sources are activated. Such second sensors generate and transmit a second microorganism input signal that corresponds to a final level of detected microorganisms after the ultraviolet light emitting are deactivated.

Notably, the independent toggling mechanism further includes a processor communicatively coupled to the sensors, and a memory communicatively coupled to the processor. The memory preferably includes software instructions that cause the processor to toggle the ultraviolet light emitting sources between the on and off modes upon detecting the triggering event. An internal power source is also housed within the cavity for supplying power to the ultraviolet light emitting sources.

In one embodiment, the software instructions includes and executes a control logic algorithm including the operational steps of: receiving the first pressure input signal from at least one of the first sensors; receiving the first microorganism input signal from at least one of the second sensors; and if the first pressure input signal and the initial microorganism input signal are associated with a corresponding one of the first and second sensors, then calculating a value of the first pressure input signal and the initial microorganism input signal by measuring a voltage level of the first pressure input signal and the initial microorganism input signal respectively.

Such a control logic algorithm may further include the operational steps of: calculating a time value directly proportional to the value of the first pressure input signal and the initial microorganism input signal; generating and transmitting a start output signal to a corresponding one of the ultraviolet light emitting sources associated with the corresponding first and second sensors; counting down to zero from the time value; and generating and transmitting a stop output signal to the corresponding ultraviolet light emitting source associated with the corresponding first and second sensors. Wherein the corresponding ultraviolet light emitting source is toggled between the on and off modes upon receiving the start and stop output signals respectively.

The present invention further includes a method for utilizing a shoe sole sanitizing device for disinfecting a bottom surface of an exterior sole of a shoe. Such a method preferably includes the chronological steps of: providing a portable platform by performing the steps of: providing a top plate provided with a pair of shoe sole-receiving sections including open bottom surfaces respectively; and providing and removably positioning a plurality of disposable transparent stratums on the open bottom surfaces respectively.

The method may further include the chronological steps of: positioning the portable platform on a ground surface; providing and aligning a plurality of ultraviolet light emitting sources beneath the shoe sole-receiving sections respectively; providing a connecting a bottom plate to the top plate wherein the bottom plate remains disposed subjacent to the shoe sole-receiving sections, wherein a cavity is formed between the top and bottom plates; positioning an exterior sole of the shoe on the shoe sole-receiving sections respectively.

The method may further include the chronological steps of: upon detecting a corresponding triggering event, independently toggling each of the ultraviolet light emitting sources between on and off modes; and the ultraviolet light emitting sources upwardly emitting an array of ultraviolet light towards the transparent stratums respectively such that the ultraviolet light arrays penetrate through the disposable transparent stratums and eradicate microorganisms deposited on the exterior surface of the shoe sole. Wherein the triggering event is defined as an initial level of microorganisms detected on the external surface of the shoe sole.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

Those skilled in the art will appreciate that the figures are not intended to be drawn to any particular scale; nor are the figures intended to illustrate every embodiment of the invention. The invention is not limited to the exemplary embodiments depicted in the figures or the shapes, relative sizes or proportions shown in the figures.

DETAILED DESCRIPTION OF THE INVENTION

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

Figure 1:
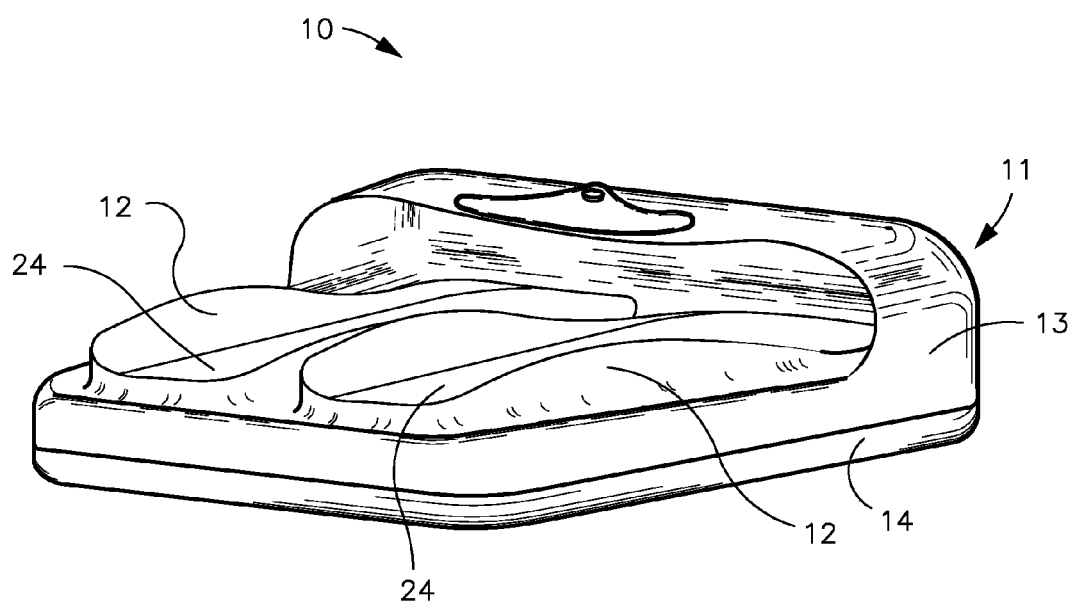
FIG. 1 is a perspective view showing a shoe sanitizing device, in accordance with the present invention.
Figure 2:
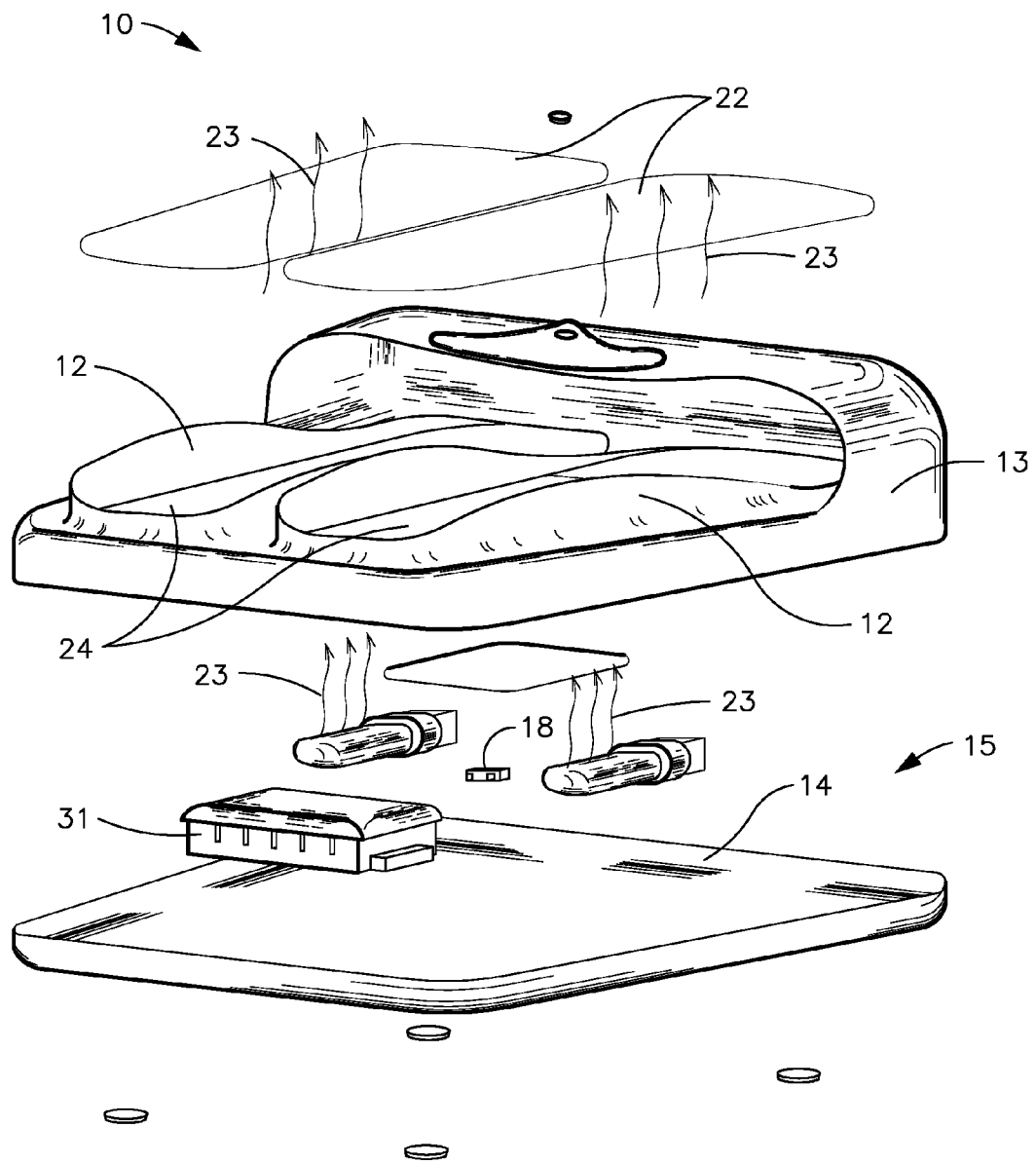
FIG. 2 is an exploded view of the shoe sanitizing device shown in FIG. 1.
Figure 3:
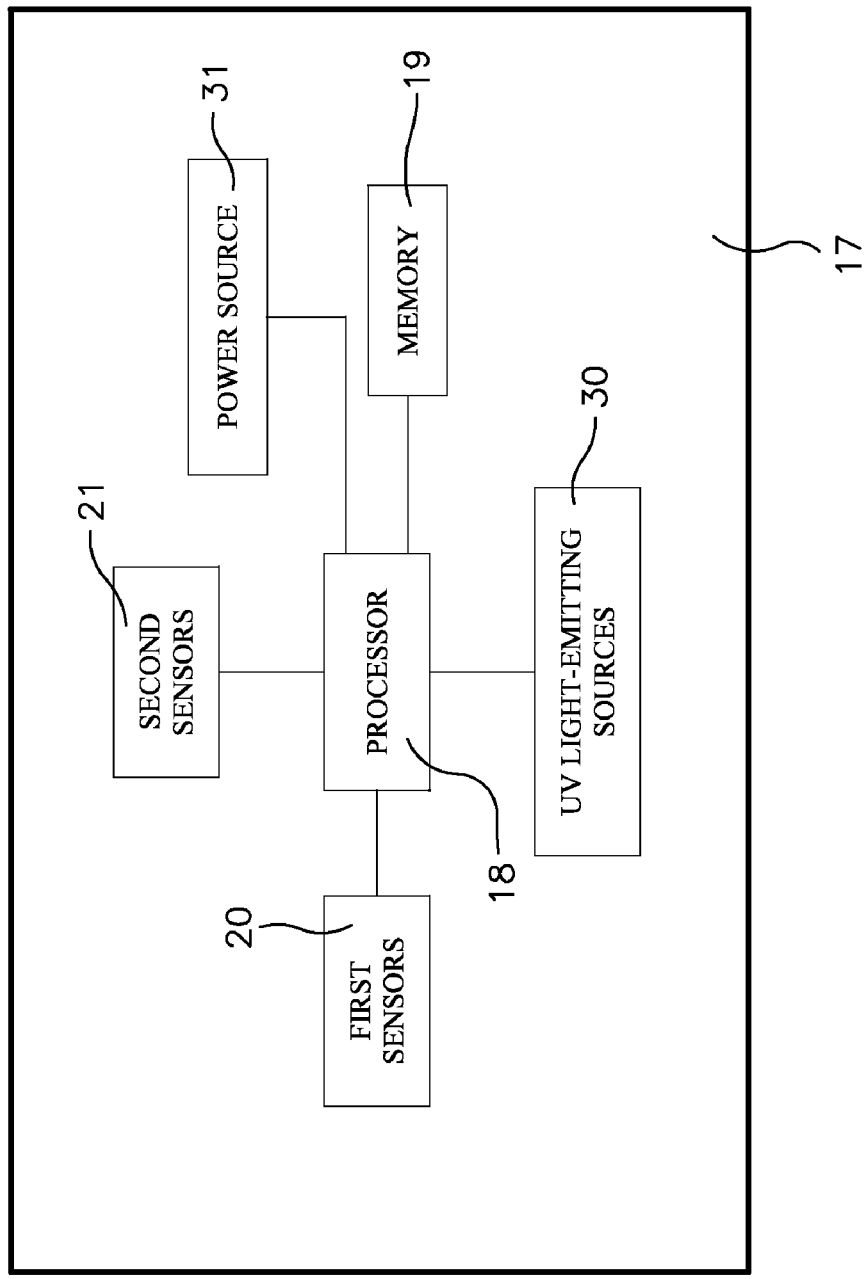
FIG. 3 is a high-level schematic block diagram showing the interrelationship between the major electronic components of the present invention.

The apparatus of this invention is referred to generally in FIGS. 1-3 by the reference numeral 10 and is intended to provide a shoe sanitizing device. It should be understood that the shoe sanitizing device 10 may be used to eradicate many different types of microorganisms found on various types of external shoe soles.

The shoe sole sanitizing device 10 preferably includes a portable platform 11 adapted to be placed on a ground surface. Such a portable platform 11 may include a top plate 13 provided with a pair of shoe sole-receiving sections 12 including open bottom surfaces 24, respectively. Each of the shoe sole-receiving sections 12 may be adapted to receive the exterior sole of the shoe (not shown) thereon.

The portable platform 11 may further include a plurality of disposable transparent stratums 22 removably positioned on the open bottom surfaces 24, respectively. A bottom plate 14 is preferably connected to the top plate 13 and remains disposed subjacent to the shoe sole-receiving sections 12. In this manner, a cavity 15 is formed between the top 13 and bottom 14 plates.

The present invention further includes a plurality of ultraviolet light emitting sources 30 aligned beneath the shoe sole-receiving sections 12, respectively. Notably, a mechanism 17 is also provided for independently toggling each of the ultraviolet light emitting sources 30 between on and off modes upon detecting a corresponding triggering event, respectively. The ultraviolet light emitting sources 30 upwardly emit an array 23 of ultraviolet light towards the transparent stratums 22 respectively such that the ultraviolet light arrays 23 penetrate through the disposable transparent stratums 22 and eradicate microorganisms deposited on the exterior surface of the shoe sole.

Notably, the triggering event may be defined as an initial level of microorganisms detected on the external surface of the shoe sole. In particular, when a high initial level of microorganisms is detected, the ultraviolet light emitting sources 30 remain active for a greater duration of time as opposed to when lower levels of microorganisms are initially detected. Such structural and functional elements solve the problem of ineffectively eradicating the microorganisms located on the external surface of the shoe sole thereby provides an unpredictable and unexpected result which is not rendered obvious by one skilled in the art.

The independent toggling mechanism 17 preferably includes a plurality of first sensors 20 situated within the platform 11. Each of the first sensors 20 generates and transmits a first pressure input signal when the shoe sole is positioned on a corresponding one of the shoe sole-receiving sections 12. Such first sensors 20 further generate and transmit a second pressure input signal when the shoe sole is removed from the corresponding shoe sole-receiving section 12.

Such first sensors 20 may include motion and/or light sensors, for example. Active and/or passive sensors may be used to react to detectable subject matter such as light, noise, radiation (e.g., heat), or changes in emitted energy, fields or beams. However, the invention is not limited to a particular type of sensor. Those skilled in the art will appreciate that other sensors may be used without departing from the scope of the invention. Examples of such other sensors include pressure sensitive mats; optical sensors configured to sense light; microwave sensors that use a Gunn diode operating within pre-set limits to transmit/flood a designated area/zone with an electronic field whereby movement in the zone disturbs the field and sets off an alarm; an ultrasonic sensor configured to react to a determined range of ultrasonic sound energy in a protected area; or any other sensor capable of providing motion detection capability in accordance with principles of the invention.

The independent toggling mechanism 17 further includes a plurality of second sensors 21 situated within the platform 11. Such second sensors 21 generate and transmit a first microorganism input signal that corresponds to an initial level of detected microorganisms before the ultraviolet light emitting sources 30 are activated. Such second sensors 21 generate and transmit a second microorganism input signal that corresponds to a final level of detected microorganisms after the ultraviolet light emitting arrays are deactivated.

Such second sensors 21 may include photometric, electrochemical, and piezoelectric biosensors, for example. Exemplary biosensors may include the biosensors developed by Oak Ridge National Laboratory's Center for Biotechnology, for example.

Both the first 20 and second sensors 21 may be designed to be linear. The output signal of such sensors 20, 21 is linearly proportional to the value of the measured property. The sensitivity is then defined as the ratio between output signal and measured property. For example, when the first 20 and second 21 sensors measure pressure and microorganism levels, respectively. The output voltage is linear and directly proportional to the detected pressure and microorganism levels because the ratio of voltage to pressure and microorganism levels is constant at all points of measurement.

Notably, the independent toggling mechanism 17 further includes a processor 18 communicatively coupled to the sensors 20, 21. A memory 19 communicatively coupled to the processor 18. The memory 19 preferably includes software instructions that cause the processor 18 to toggle the ultraviolet light emitting sources 30 between the on and off modes upon detecting the triggering event. An internal power source 31 is also housed within the cavity 15 for supplying power to the ultraviolet light emitting sources 30.

The processor 18 may include a microprocessor or other devices capable of being programmed or configured to perform computations and instruction processing in accordance with the invention. Such other devices may include microcontrollers, digital signal processors (DSP), Complex Programmable Logic Device (CPLD), Field Programmable Gate Arrays (FPGA), application-specific integrated circuits (ASIC), discrete gate logic, and/or other integrated circuits, hardware or firmware in lieu of or in addition to a microprocessor.

Functions and process steps described herein may be performed using programmed computer devices 10 and related hardware, peripherals, equipment and networks. When programmed, the computing devices are configured to perform functions and carry out steps in accordance with principles of the invention. Such programming may comprise operating systems, software applications, software modules, scripts, files, data, digital signal processors (DSP), application-specific integrated circuit (ASIC), discrete gate logic, or other hardware, firmware, or any conventional programmable software, collectively referred to herein as a module.

The memory 19 includes programmable software instructions that are executed by the processor 18. In particular, the programmable software instructions include a plurality of chronological operating steps that define a control logic algorithm for performing the intended functions of the present invention. Such software instructions may be written in a variety of computer program languages such as C++, Fortran and Pascal, for example. One skilled in the art understands that such software instructions may contain various Boolean logic processes that perform the intended function of the present invention. Therefore, the specific source or object code of the software program is not intended to be a limiting factor in executing the present invention's intended function.

The memory 19, which enables storage of data and programs, may include RAM, ROM, flash memory 19 and any other form of readable and writable storage medium known in the art or hereafter developed. The memory 19 may be a separate component or an integral part of another component such as processor 18.

In one embodiment, the software instructions includes and executes a control logic algorithm including the operational steps of: receiving the first pressure input signal from at least one of the first sensors 20; receiving the first microorganism input signal from at least one of the second sensors 21; and if the first pressure input signal and the initial microorganism input signal are associated with a corresponding one of the first and second sensors 20, 21, then calculating a value of the first pressure input signal and the initial microorganism input signal by measuring a voltage level of the first pressure input signal and the initial microorganism input signal, respectively.

Such a control logic algorithm may further include the operational steps of: calculating a time value directly proportional to the value of the first pressure input signal and the initial microorganism input signal; generating and transmitting a start output signal to a corresponding one of the ultraviolet light emitting sources 30 associated with the corresponding first and second sensors 20, 21; counting down to zero from the time value; and generating and transmitting a stop output signal to the corresponding ultraviolet light emitting source 30 associated with the corresponding first and second sensors 20, 21. Wherein the corresponding ultraviolet light emitting source 30 is toggled between the on and off modes upon receiving the start and stop output signals respectively.

The present invention further includes a method for utilizing a shoe sole sanitizing device 10 for disinfecting a bottom surface of an exterior sole of a shoe. Such a method preferably includes the chronological steps of: providing a portable platform 11 by performing the steps of: providing a top plate 13 provided with a pair of shoe sole-receiving sections 12 including open bottom surfaces 24 respectively; and providing and removably positioning a plurality of disposable transparent stratums 22 on the open bottom surfaces 24, respectively.

The method may further include the chronological steps of: positioning the portable platform 11 on a ground surface; providing and aligning a plurality of ultraviolet light emitting sources 30 beneath the shoe sole-receiving sections 12, respectively; providing a connecting a bottom plate 14 to the top plate 13 wherein the bottom plate 14 remains disposed subjacent to the shoe sole-receiving sections 12, wherein a cavity 15 is formed between the top and bottom plates 14; and positioning an exterior sole of the shoe on the shoe sole-receiving sections 12, respectively.

The method may further include the chronological steps of: upon detecting a corresponding triggering event, independently toggling each of the ultraviolet light emitting sources 30 between on and off modes; and the ultraviolet light emitting sources 30 upwardly emitting an array 23 of ultraviolet light towards the transparent stratums 22 respectively such that the ultraviolet light arrays 23 penetrate through the disposable transparent stratums 22 and eradicate microorganisms deposited on the exterior surface of the shoe sole. Wherein the triggering event is defined as an initial level of microorganisms detected on the external surface of the shoe sole.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A shoe sole sanitizing device for disinfecting a bottom surface of an exterior sole of a shoe, said shoe sole sanitizing device comprising:
   a platform including
      a top plate provided with a pair of shoe sole-receiving sections including open bottom surfaces respectively, each of said shoe sole-receiving sections being adapted to receive the exterior sole of the shoe thereon,
      a plurality of disposable transparent stratums removably positioned on said open bottom surfaces respectively,
      a bottom plate connected to said top plate and remaining disposed subjacent to said shoe sole-receiving sections, and
      a cavity formed between said top and bottom plates;
   a plurality of ultraviolet light emitting sources; and
   means for independently toggling each of said ultraviolet light emitting sources between on and off modes upon detecting a corresponding triggering event respectively;
   wherein said ultraviolet light emitting sources upwardly emit an array of ultraviolet light towards said transparent stratums respectively such that said ultraviolet light arrays penetrate through said disposable transparent stratums and eradicate microorganisms deposited on the exterior surface of the shoe sole;
   wherein said triggering event is an initial level of microorganisms detected on the external surface of the shoe sole.

2. The shoe sole sanitizing device of claim 1, wherein said independent toggling means comprises:
   a plurality of first sensors situated within said platform, each of said first sensors generating and transmitting a first pressure input signal when the shoe sole is positioned on a corresponding one of said shoe sole-receiving sections, each of said first sensors further generating and transmitting a second pressure input signal when the shoe sole is removed from the corresponding shoe sole-receiving section;
   a plurality of second sensors situated within said platform, each of said second sensors generating and transmitting a first microorganism input signal that corresponds to an initial level of detected microorganisms before said ultraviolet light emitting sources are activated, each of said second sensors generating and transmitting a second microorganism input signal that corresponds to a final level of detected microorganisms after said ultraviolet light emitting are deactivated.

3. The shoe sole sanitizing device of claim 2, wherein said independent toggling means further comprises:
   a processor communicatively coupled to said sensors;
   a memory communicatively coupled to said processor, said memory including software instructions that cause said processor to toggle said ultraviolet light emitting sources between said on and off modes; and
   an internal power source housed within said cavity for supplying power to said ultraviolet light emitting sources.

4. The shoe sole sanitizing device of claim 3, wherein said software instructions comprises and executes a control logic algorithm including the operational steps of:
   i. receiving said first pressure input signal from at least one of said first sensors;
   ii. receiving said first microorganism input signal from at least one of said second sensors; and
   iii. if said first pressure input signal and said initial microorganism input signal are associated with a corresponding one of said first and second sensors, then calculating a value of said first pressure input signal and said initial microorganism input signal by measuring a voltage level of said first pressure input signal and said initial microorganism input signal respectively.

5. The shoe sole sanitizing device of claim 4, wherein control logic algorithm further comprises the operational steps of:
   i. calculating a time value directly proportional to said value of said first pressure input signal and said initial microorganism input signal;
   ii. generating and transmitting a start output signal to a corresponding one of said ultraviolet light emitting sources associated with said corresponding first and second sensors;
   iii. counting down to zero from said time value; and
   iv. generating and transmitting a stop output signal to said corresponding ultraviolet light emitting source associated with said corresponding first and second sensors;

wherein said corresponding ultraviolet light emitting source is toggled between said on and off modes upon receiving said start and stop output signals respectively.

6. The shoe sole sanitizing device of claim 2, wherein said second sensors are biosensors.

7. A shoe sole sanitizing device for disinfecting a bottom surface of an exterior sole of a shoe, said shoe sole sanitizing device comprising:
- a portable platform adapted to be placed on a ground surface, said portable platform including
  - a top plate provided with a pair of shoe sole-receiving sections including open bottom surfaces respectively, each of said shoe sole-receiving sections being adapted to receive the exterior sole of the shoe thereon,
  - a plurality of disposable transparent stratums removably positioned on said open bottom surfaces respectively,
  - a bottom plate connected to said top plate and remaining disposed subjacent to said shoe sole-receiving sections, and
  - a cavity formed between said top and bottom plates;
- a plurality of ultraviolet light emitting sources aligned beneath said shoe sole-receiving sections respectively; and
- means for independently toggling each of said ultraviolet light emitting sources between on and off modes upon detecting a corresponding triggering event respectively;
- wherein said ultraviolet light emitting sources upwardly emit an array of ultraviolet light towards said transparent stratums respectively such that said ultraviolet light arrays penetrate through said disposable transparent stratums and eradicate microorganisms deposited on the exterior surface of the shoe sole;
- wherein said triggering event is an initial level of microorganisms detected on the external surface of the shoe sole.

8. The shoe sole sanitizing device of claim 7, wherein said independent toggling means comprises:
- a plurality of first sensors situated within said platform, each of said first sensors generating and transmitting a first pressure input signal when the shoe sole is positioned on a corresponding one of said shoe sole-receiving sections, each of said first sensors further generating and transmitting a second pressure input signal when the shoe sole is removed from the corresponding shoe sole-receiving section;
- a plurality of second sensors situated within said platform, each of said second sensors generating and transmitting a first microorganism input signal that corresponds to an initial level of detected microorganisms before said ultraviolet light emitting sources are activated, each of said second sensors generating and transmitting a second microorganism input signal that corresponds to a final level of detected microorganisms after said ultraviolet light emitting are deactivated.

9. The shoe sole sanitizing device of claim 8, wherein said independent toggling means further comprises:
- a processor communicatively coupled to said sensors;
- a memory communicatively coupled to said processor, said memory including software instructions that cause said processor to toggle said ultraviolet light emitting sources between said on and off modes; and
- an internal power source housed within said cavity for supplying power to said ultraviolet light emitting sources.

10. The shoe sole sanitizing device of claim 9, wherein said software instructions comprises and executes a control logic algorithm including the operational steps of:
  i. receiving said first pressure input signal from at least one of said first sensors;
  ii. receiving said first microorganism input signal from at least one of said second sensors; and
  iii. if said first pressure input signal and said initial microorganism input signal are associated with a corresponding one of said first and second sensors, then calculating a value of said first pressure input signal and said initial microorganism input signal by measuring a voltage level of said first pressure input signal and said initial microorganism input signal respectively.

11. The shoe sole sanitizing device of claim 10, wherein control logic algorithm further comprises the operational steps of:
  i. calculating a time value directly proportional to said value of said first pressure input signal and said initial microorganism input signal;
  ii. generating and transmitting a start output signal to a corresponding one of said ultraviolet light emitting sources associated with said corresponding first and second sensors;
  iii. counting down to zero from said time value; and
  iv. generating and transmitting a stop output signal to said corresponding ultraviolet light emitting source associated with said corresponding first and second sensors;
- wherein said corresponding ultraviolet light emitting source is toggled between said on and off modes upon receiving said start and stop output signals respectively.

12. The shoe sole sanitizing device of claim 8, wherein said second sensors are biosensors.

* * * * *